US00PP36829P2

(12) United States Plant Patent
van Noort

(10) Patent No.: US PP36,829 P2
(45) Date of Patent: Jul. 15, 2025

(54) ***GERANIUM* PLANT NAMED 'MVNG1811'**

(50) Latin Name: *Geranium sanguineum*
Varietal Denomination: MVNG1811

(71) Applicant: Marco van Noort, Warmond (NL)

(72) Inventor: Marco van Noort, Warmond (NL)

(73) Assignee: MARCO VAN NOORT BREEDING B.V., Warmond (NL)

( * ) Notice: Subject to any disclaimer, the term of this patent is extended or adjusted under 35 U.S.C. 154(b) by 0 days.

(21) Appl. No.: 19/048,917

(22) Filed: Feb. 8, 2025

(51) Int. Cl.
*A01H 5/02* (2018.01)
*A01H 6/42* (2018.01)

(52) U.S. Cl.
USPC ..... Plt./324

(58) Field of Classification Search
USPC ..... Plt./324
See application file for complete search history.

*Primary Examiner* — Susan McCormick Ewoldt
(74) *Attorney, Agent, or Firm* — Penny J. Aguirre

(57) ABSTRACT

A new cultivar of *Geranium sanguineum* plant named 'MVNG1811' that is characterized by its flowers that are large in size and light pink in color, its floriferious blooming habit, its re-blooming throughout the season, its flowering season that commences early in the season, and its compact and mounded plant habit.

2 Drawing Sheets

Botanical classification: *Geranium sanguineum.*
Cultivar designation: 'MVNG1811'.

CROSS-REFERENCE TO RELATED APPLICATIONS

This application is related to a European plant breeders' rights application filed on Sep. 1, 2023, application No. 2023/1838. The Information for the Plant Breeders' Rights Application was received directly from the Inventor. This application is also co-pending with a U.S. Plant Patent Applications filed for plants derived from the same breeding program that are entitled *Geranium* Plant Named 'MVNG1901' (U.S. Plant patent application Ser. No. 19/048,919) and *Geranium* Plant Named 'MVNG1905' (U.S. Plant patent application Ser. No. 19/048,920).

BACKGROUND OF THE INVENTION

The present invention relates to a new and distinct cultivar of *Geranium* plant, botanically known as *Geranium sanguineum* 'MVNG1811' and will be referred to hereafter by its cultivar name, 'MVNG1811'. 'MVNG1811' is a new cultivar of herbaceous perennial grown for use as a garden plant.

'MVNG1811' arose from an on going breeding program conducted by the Inventor in Warmond, The Netherlands. The objectives of the breeding program is to develop new cultivars of *Geranium* that have healthy growth habits, re-blooming habits, and resistance to higher temperatures in dryer locations.

'MVNG1811' originated as a seedling that arose from seed planted from open pollination of an unnamed and unpatented plant of *Geranium sanguineum* var. *striatum* in May of 2020. The male parent is therefore unknown. 'MVNG1811' was selected as a single unique plant in June of 2021 from the resulting seedlings.

Asexual propagation of the new cultivar was first accomplished by stem cuttings under the direction of the Inventor in Warmond, The Netherlands in December of 2023. Asexual propagation by stem cuttings and tissue culture tissue culture using meristematic tissue has determined that the characteristics of the new cultivar are stable and are reproduced true to type in successive generations.

SUMMARY OF THE INVENTION

The following traits have been repeatedly observed and represent the characteristics of 'MVNG1811'. These attributes in combination distinguish 'MVNG1811' as a new and distinct cultivar of *Geranium.*

1. 'MVNG1811' exhibits flowers that are large in size and light pink in color.
2. 'MVNG1811' exhibits a floriferous blooming habit.
3. 'MVNG1811' exhibits re-blooming throughout the season.
4. 'MVNG1811' exhibits a flowering season that commences early in the season.
5. 'MVNG1811' exhibits a compact and mounded plant habit.

The female parent differs from 'MVNG1811' in having a later and shorter flowering season and flowers that are smaller in size, and in being less floriferous. 'MVNG1811' can be most closely compared to the *Geranium* cultivars 'Striatum' (not patented) and 'Apfelblute' (not patented). 'Striatum' is similar to 'MVNG1811' in having pink flowers. 'Striatum' differs from 'MVNG1811' in having a later flowering period, a less floriferous blooming habit, a less compact plant habit, and flowers that are smaller in size. 'Apfelblute' is similar to 'MVNG1811' in having pink flowers. 'Apfelblute' differs from 'MVNG1811' in having a later flowering period and flowers that are smaller in size, and in being more difficult to propogate.

'MVNG1811' can also be compared to the co-pending cultivars of *Geranium*; 'MVNG1901' and 'MVNG1905'. 'MVNG1901' differs from 'MVNG1811' in violet-pink flowers. 'MVNG1905' differs from 'MVNG1811' in having flowers that open pink in color and then change to violet-purple in color.

BRIEF DESCRIPTION OF THE DRAWINGS

The accompanying color photographs illustrate the overall appearance and distinct characteristics of the new *Geranium*. The photographs were taken of one year-old plants of 'MVNG1811' as grown in a 17-cm circular container outdoors in Warmond, The Netherlands.

The photograph in FIG. 1 provides a top view of 'MVNG1811' in bloom.

Figure 1:
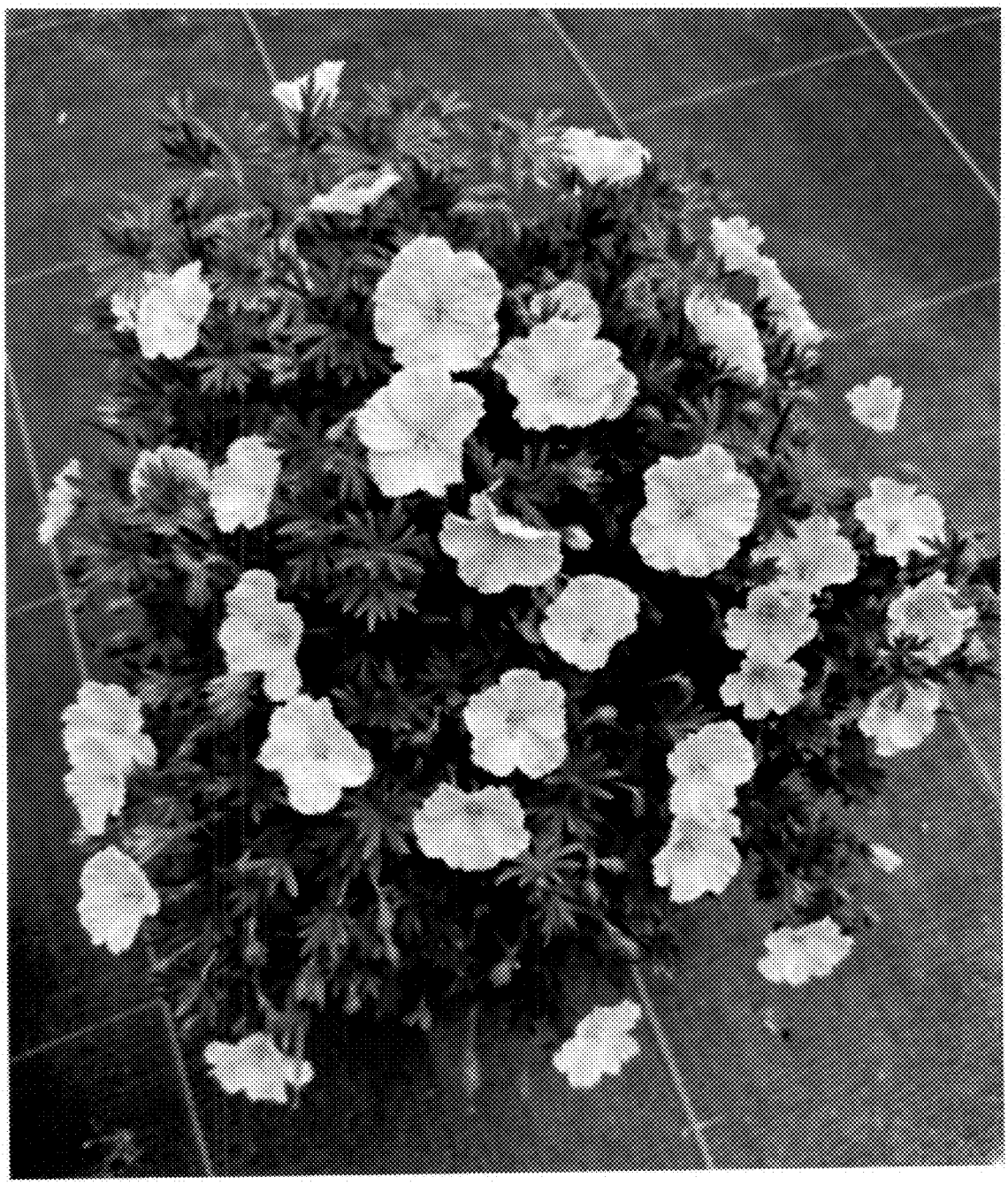
Figure 2:
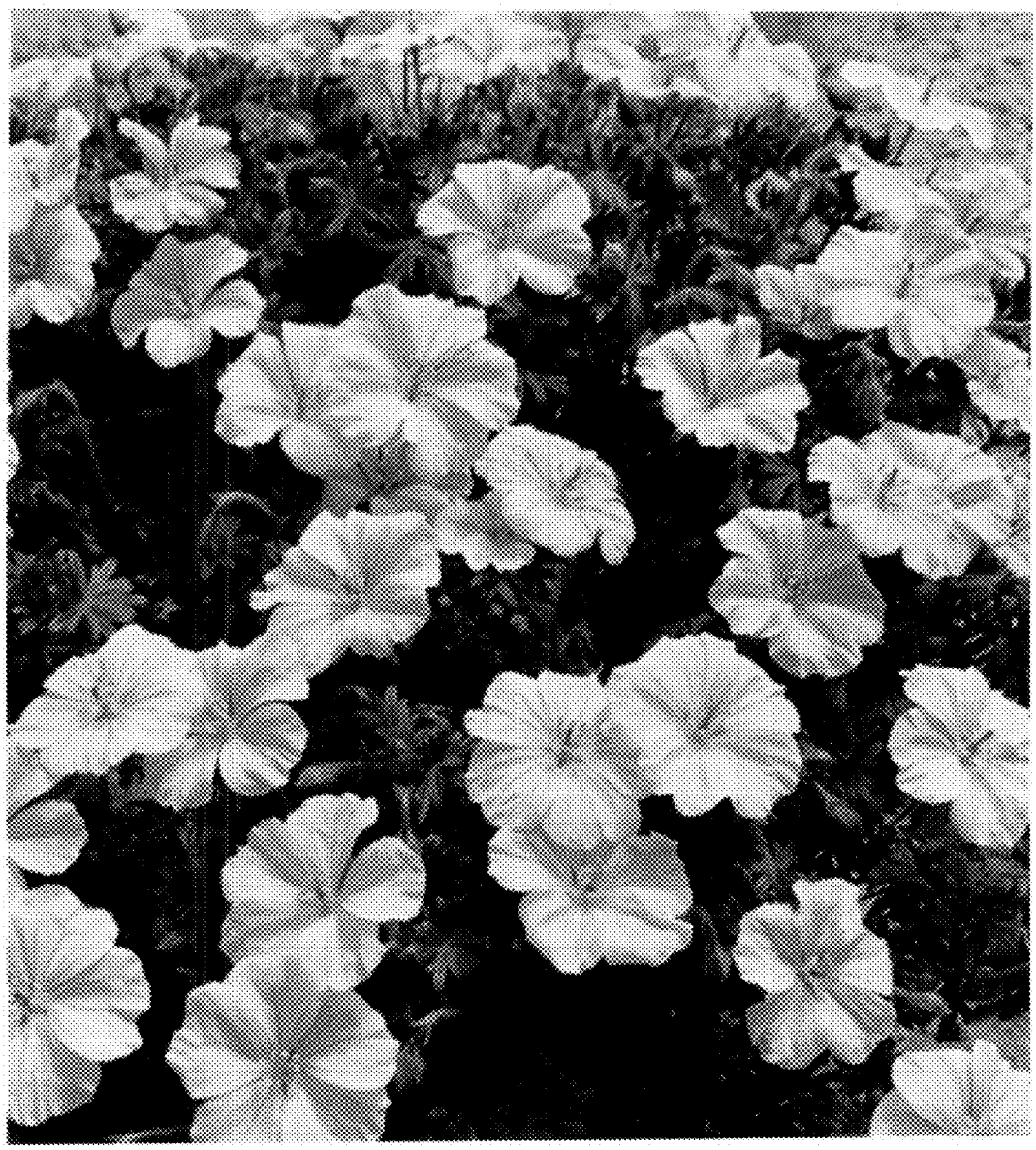

The photograph in FIG. 2 provides a close-up view of the flowers of 'MVNG1811'.

The colors in the photographs are as close as possible with the digital photography and printing techniques utilized and the color codes in the detailed botanical description accurately describe the colors of the new *Geranium*.

DETAILED BOTANICAL DESCRIPTION OF THE PLANT

The following is a detailed description of one year-old plants of the new cultivar as grown in a 17-cm circular container outdoors in Warmond, The Netherlands. The phenotype of the new cultivar may vary with variations in environmental, climatic, and cultural conditions, as it has not been tested under all possible environmental conditions. The color determination is in accordance with the 2015 6$^{th}$ edition Colour Chart of The Royal Horticultural Society, London, England, except where general color terms of ordinary dictionary significance are used.

General characteristics:

*Blooming period*.—Spring into late summer in The Netherlands.

*Plant type*.—Herbaceous perennial.

*Plant habit*.—Compact mound, broadly spreading.

*Height and spread*.—Reaches about 14 cm in height and 43.3 cm in spread as a 1-year-old plant grown in a container.

*Hardiness*.—At least in U.S.D.A. Zones 5 to 9.

*Diseases and pests*.—No susceptiblity or resistance to disease or pests has been observed.

*Root description*.—Slightly fleshy, overall average diameter of the root system is 2 mm, both shallow and moderately deep distribution into the soil, moderate density, moderately branched, smooth and glabrous surfaces, 164C in color.

*Root development*.—Average of 6 to 8 weeks for root initiation, 12 to 14 weeks to produce a rooted cutting.

*Growth rate*.—Moderately vigorous.

*Growth habit*.—Strong.

*Propagation*.—Stem cuttings and tissue culture.

Branch description:

*Branch size*.—Average of 15.8 cm in length and 2 mm in width.

*Branch shape*.—Round.

*Branch strength*.—Moderately strong.

*Branch color*.—Young; 144B, mature; 144B, tinged 165C.

*Branch surface*.—Slightly glossy and moderately covered with short hairs, average of 1.5 mm in length and too small to measure color.

*Internode length*.—Average of 2.3 cm.

*Branching habit*.—Freely branched, average of 16 main branches, 32 lateral branches.

Foliage description:

*Leaf shape*.—Reniform (overall shape), palmately cleft with an average of 7 lobes.

*Leaf division*.—Simple.

*Leaf base*.—Hastate, lobes free to touching.

*Leaf apex*.—Acute.

*Leaf venation*.—Palmate, both surfaces 148B in color.

*Leaf margins*.—Lanciniate.

*Leaf aspect*.—Average of 70° to stem.

*Leaf lobes*.—Sinuses are deep, sinus orientation is convergent.

*Leaf attachment*.—Petiolate.

*Leaf arrangement*.—Opposite.

*Leaf surface*.—Both surfaces non-rugose, upper surface slightly glossy, lower surface very slightly glossy, covered with short hairs; an average of 0.5 mm in length, too small to measure color.

*Leaf color*.—Young upper surface; 137B, young lower surface; 138B, mature upper surface; NN137C, mature lower surface; a blend of 138B and 147B.

*Leaf size*.—Average of 3 cm in length and width.

*Leaf quantity*.—Average of 14 (7 pairs) per lateral branch.

*Petioles*.—Average of 2 cm in length and 1.2 mm in width, upper surface color 144A to 144B, lower surface color 144B, both surfaces are slightly glossy, densely covered with short hairs an average of 1.25 mm in length and N155A, high strength.

*Stipules*.—2 leafy stipules, present at the base of the leaves, broad deltoid in shape, apex is broadly acute, base broad cuneate, average of 3 mm in length and width, 164A in color.

Flower description:

*Inflorescence type*.—Axillary, solitary.

*Lastingness of flowers*.—Average of 7 days, self cleaning.

*Flowers*.—Up to 40 per plant, rotate, single, average of 4.2 cm and diameter, 1.1 cm in depth, primarily facing upward to outward.

*Flower fragrance*.—None.

*Flower bud*.—Up to 360 per plant, an average of 8 mm in length, 4 mm in width, color; 138B, veined 138A, elliptic in shape, surface is densely covered with short glandular hairs an average of 1 mm in length and a blend of N155A to 157D in color.

*Petals*.—5, rotate in arrangement, 1 whorl, obcordate in shape, narrow cuneate base, broadly retuse apex, entire margins, surfaces are glabrous, velvety, and matte, average of 2.1 cm in length, 2 cm in width, color: when opening upper surface; 75B, veined N74B, when opening lower surface; a blend of 75B to 75C, veined N74B, when fully open upper and lower surface; 75B to 75C.

*Calyx*.—Rotate, average of 7 mm in length and 1.8 cm in width.

*Sepals*.—Average of 5, ovate in shape, entire margins, mucronate apex, cuneate base, average of 1.1 cm length, 4.5 mm in width, upper surface glabrous, smooth, moderately glossy, lower surface glabrous, smooth, matte and densely covered with short hairs 1 mm in length, a blend of N155A and 156D in color, color: when opening upper surface; 138B, margins transparent 157D, veins 138A, when opening lower surface; 143B, margins 157D, veins 146B, when fully open upper surface; 138B, margins 157D, veins 138A, not fading, when fully open lower surface; 144A, margins 157D, veins 143A. not fading.

*Peduncles*.—Average of 6.5 cm in length and 1 mm in diameter, moderately to strong, held in a 30° angle to lateral branch, 143B in color, surfaces are moderately glossy and densely covered with short hairs, average of 1 mm in length and a blend of NN155D and 157D in color.

*Pedicels*.—None.

*Floral bracts*.—Two bracts are placed at the top of each flower, narrow deltoid in shape, concave, average of 3 mm in length, 1 mm in width, entire margin, narrow acuminate apex, cuneate base, upper surface smooth and glabrous, lower surface densely covered with short hairs average of 0.5 mm in length, NN155D in color, both surfaces are 165B in color, main vein 165A in color.

Reproductive organs:

*Gynoecium*.—Pistil; 1, average of 7 mm in length, stigmas; 5, curled, 2 mm in length, 4 mm in diameter, N170C in color, style; average of 5 mm in length, color; N170C, base 147B, ovary is 143B in color.

*Androecium*.—Stamens; 10, anthers; narrow oblong in shape, 2 mm in length, 0.75 mm in width, 59D in color, filaments; 6 mm in length, 68D in color, pollen is moderate in quantity and 9D in color.

*Fruit/seeds*.—Fruit present; average of 3 per plant, 3.8 cm in length, 4.5 mm in diameter, color; 143C, base 144C, persistent styles and stigmas 174D, surface is moderately covered with very short hairs; an average of 0.75 mm in length, too small to measure color, seeds; none observed.

It is claimed:

1. A new and distinct cultivar of *Geranium* plant named 'MVNG1811' as herein illustrated and described.

* * * * *